US009562905B2

(12) United States Patent
Ruddock et al.

(10) Patent No.: US 9,562,905 B2
(45) Date of Patent: Feb. 7, 2017

(54) METHOD FOR DETECTION OF, OR THE RISK OF, BLADDER CANCER

(75) Inventors: Mark W. Ruddock, Crumlin (GB);
Cherith N. Reid, Crumlin (GB);
Kathleen Williamson, Belfast (GB);
John V. Lamont, Crumlin (GB);
Stephen P. Fitzgerald, Crumlin (GB)

(73) Assignee: RANDOX LABORATORIES LIMITED (GB)

( * ) Notice: Subject to any disclaimer, the term of this patent is extended or adjusted under 35 U.S.C. 154(b) by 4 days.

(21) Appl. No.: 13/386,228

(22) PCT Filed: Jul. 29, 2010

(86) PCT No.: PCT/GB2010/051255
§ 371 (c)(1),
(2), (4) Date: Feb. 15, 2012

(87) PCT Pub. No.: WO2011/012901
PCT Pub. Date: Feb. 3, 2011

(65) Prior Publication Data
US 2012/0135886 A1 May 31, 2012

(30) Foreign Application Priority Data

Jul. 29, 2009 (GB) .................................. 0913249.9
Sep. 15, 2009 (GB) .................................. 0916193.6

(51) Int. Cl.
*G01N 33/567* (2006.01)
*G01N 33/574* (2006.01)

(52) U.S. Cl.
CPC ..... *G01N 33/57407* (2013.01); *G01N 2800/34* (2013.01)

(58) Field of Classification Search
None
See application file for complete search history.

(56) References Cited

U.S. PATENT DOCUMENTS

2009/0221010 A1* 9/2009 Elting et al. .................. 435/7.94
2012/0231963 A1  9/2012 Huang et al.

FOREIGN PATENT DOCUMENTS

| EP | 1477803 | | 11/2004 | |
|---|---|---|---|---|
| GB | 2324866 | | 11/1998 | |
| IT | WO/2005/043165 | * | 5/2005 | ........... G01N 33/574 |
| WO | WO 2009/017475 | | 2/2009 | |

OTHER PUBLICATIONS

Saied et al (World Journal of Surgical Oncology 2007, vol. 5, No. 4, pp. 1-6, published Jan. 15, 2007).*
Ayyildiz et al (Nuclear Matrix Protein 22 (NMP22) in the Bladder Tumor Comparison with the Findings of Cystoscopy, Stage and Grade of the Tumor, Turk Uroloji Dergisi: vol. 29(3): pp. 277-284, 2003;Abstract only in English language).*
Tetu reference entitled "Diagnosis of urothelial carcinoma from urine" (Modern Pathology: Jun. 2009 vol. 22, Issue S2, pp. S53-S59).*
Alvarez et al in "Bladder cancer biomarkers: current developments and future implementation" (Curr Opin Urol vol. 17, pp. 341-346, 2007).*
Rodgers et al in "Diagnostic tests used in the investigation of adult haematuria: a systematic review" (Journal Compilation 2006: pp. 1154-1160).*
Notification of Transmittal of the International Search Report of the International Searching Authority mailed Feb. 3, 2011 in International Application No. PCT/GB2010/051255.
Notification Concerning Transmittal of International Preliminary Report on Patentability mailed Feb. 9, 2012 in International Application No. PCT/GB2010/051255.
Chen, L., et al., "Advancements in Bladder Cancer Markers," Journal of Clinicaloncology, Tianjin Shi Yixue Zazhishe, Tianjin, Ch, vol. 35, No. 8, Jan. 1, 2008, pp. 470-473, XP009138722.
Egawa, S., et al., "Search for Biomarkers of Aggressiveness in Bladder Cancer," European Urology, Elsevier B.V., NL LNKD-DOI:10.1016/J.Eururo.2006.01.059, vol. 50, No. 1., Jul. 1, 2006, pp. 20-22, XP025019891.
Huben, R., et al., "Tumor Markers in Bladder Cancer," Supplemental to Urology, vol. 23, No. 3, Mar. 1, 1984, pp. 10-14, XP027012054.
Voorzanger-Rousselot, et al., "Biochemical Markers in Oncology. Part I: Molecular Basis. Part II: Clinical Uses" Cancer Treatment Reviews, US LNKD-DOI:10.1016/J.CTRV.2007.01.008, vol. 33, No. 3, May 1, 2007, pp. 230-283, XP022090048.
Williamson, K., et al., "48LBA Algorithmic Classifiers to Diagnose Bladder Cancer," European Journal of Cancer, Supplement, Pergamon, Oxford, GB LNKD-DOI:10.1016/51359-6349(09)72083-X, vol. 7, No. 3, Sep. 1, 2009, p. 21, XP026629205.
Helal I et al., "Comparison of C-Reactive Protein and High-Sensitivity C-Reactive Protein Levels in Patients on Hemodialysis" *Saudi Journal of Kidney Diseases and Transplantation*, 2012, 23(3):477-483.
Odisho AY et al., "Reflex ImmunoCyt Testing for the Dialysis of Bladder Cancer in Patients with Atypical Urine Cytology" *European Urology*, 2013, 63:936-940.
Williamson K et al., "Algorithmic classifiers to diagnose bladder cancer" *European Journal of Cancer, Supplement*, Abstract No. 48LBA, published Sep. 20, 2009, 7(3):21.
European Examination Report dated Jun. 23, 2014, received in related EPO Application No. 10737623.8.
(Continued)

*Primary Examiner* — Catherine S Hibbert
(74) *Attorney, Agent, or Firm* — Saliwanchik, Lloyd & Eisenschenk

(57) ABSTRACT

Methods for the detection of, or the risk of, bladder cancer in a patient, comprising assaying for the presence of a combination of at least two biomarkers selected from CEA, VEGF, IL-8, NGAL, NSE, IL-2, EGF, TM, d-Dimer, MMP-9, IL-6, IL-4, MMP-9/NGAL, FAS, CRP, TUP and NMP22 in one or more samples isolated from a patient wherein detecting the presence of a combination of at least two biomarkers in the one or more samples indicates the presence or risk of bladder cancer.

13 Claims, 3 Drawing Sheets

(56) References Cited

OTHER PUBLICATIONS

Abogunrin, F. et al. "The impact of biomarkers in multivariate algorithms for bladder cancer diagnosis in patients with hematuria" *Cancer,* 2012 (Epub Sep. 14, 2011), 118(10):2641-2650.
Zweig, M. and Campbell, G. et al. "Receiver-Operating Characteristic (ROC) Plots: A Fundamental Evaluation Tool in Clinical Medicine" *Clin. Chem.,* 1993, 39(4):561-577.
Emmert-Streib, F. et al. "Collectives of diagnostic biomarkers identify high-risk subpopulations of hematuria patients: exploiting heterogeneity in large-scale biomarker data" *BMC Medicine,* Jan. 17, 2013, 11:1-15.

* cited by examiner

FIG. 1

| Variable | TCCB (SD) | Controls (SD) | Mean difference (95% CI) | p value |
|---|---|---|---|---|
| Age | 69.2 (8.4) | 54.3 (18.4) | -14.9 (-19.5 to -10.4) | 0.001 |
| Cigarettes/day | 16.0 (17.6) | 9.7 (13.2) | -6.3 (-11.2 to -1.5) | 0.011 |
| Smoking yrs | 27.0 (19.5) | 13.6 (17.1) | -13.4 (-19.2 to -7.6) | 0.001 |
| Alcohol | 4.6 (8.3) | 4.9 (7.6) | 0.3 (-2.2 to 2.8) | 0.830 |
| Protein | -1.2 (0.6) | -1.4 (0.6) | -0.2 (-0.4 to -0.0) | 0.012 |
| Creatinine | 97.1 (28.1) | 97.8 (31.7) | 0.7 (-8.7 to 10.1) | 0.884 |
| Osmolality | 528.4 (198.5) | 558.6 (232.9) | 30.2 (-37.5 to 97.8) | 0.380 |
| BTA | -0.2 (0.6) | -0.5 (0.5) | -0.3 (-0.5 to -0.1) | 0.001 |
| CEA | 0.3 (0.3) | 0.1 (0.3) | -0.2 (-0.3 to -0.1) | 0.001 |
| CK18 | -0.7 (0.2) | -0.7 (0.2) | -0.0 (-0.1 to 0.1) | 0.818 |
| CRP | -0.1 (0.1) | 0.0 (0.2) | 0.1 (0.0 to 0.1) | 0.001 |
| D-Dimer | 1.3 (1.0) | 0.7 (0.8) | -0.5 (-0.8 to -0.3) | 0.001 |
| EGF | -0.4 (0.2) | -0.3 (0.2) | 0.1 (0.0 to 0.2) | 0.021 |
| FAS | -0.7 (0.3) | -0.8 (0.3) | -0.1 (-0.2 to -0.0) | 0.011 |
| FPSA | -1.0 (0.4) | -1.1 (0.3) | -0.2 (-0.3 to -0.0) | 0.011 |
| HA | -0.1 (0.3) | -0.0 (0.2) | 0.1 (-0.0 to 0.1) | 0.124 |
| IL-1α | 0.6 (0.8) | 0.2 (0.5) | -0.4 (-0.6 to -0.2) | 0.001 |
| IL-1β | 0.4 (0.6) | 0.3 (0.4) | -0.2 (-0.3 to -0.0) | 0.059 |
| IL-2 | 0.8 (0.1) | 0.8 (0.1) | -0.0 (-0.1 to -0.0) | 0.008 |
| IL-4 | 0.6 (0.1) | 0.6 (0.1) | -0.0 (-0.1 to -0.0) | 0.065 |
| IL-6 | 0.9 (1.0) | 0.3 (0.9) | -0.6 (-0.9 to -0.3) | 0.001 |
| IL-8 | 2.3 (1.0) | 1.6 (0.9) | -0.7 (-1.0 to -0.4) | 0.001 |
| MCP-1 | 2.1 (0.5) | 2.0 (0.5) | -0.1 (-0.2 to -0.0) | 0.188 |
| MMP-9 | 0.6 (0.4) | 0.6 (0.3) | -0.0 (-0.1 to 0.1) | 0.592 |
| MMP-9/NGAL | -0.9 (0.3) | -1.0 (0.2) | -0.1 (-0.2 to -0.0) | 0.010 |
| NGAL | 2.3 (0.5) | 2.2 (0.4) | -0.1 (-0.2 to 0.1) | 0.282 |
| NSE | -0.3 (0.5) | -0.4 (0.6) | -0.1 (-0.3 to 0.1) | 0.447 |
| TM | 0.6 (0.3) | 0.6 (0.3) | 0.0 (-0.1 to 0.1) | 0.408 |
| TNFα | 1.0 (0.1) | 1.0 (0.2) | -0.0 (-0.1 to 0.0) | 0.631 |
| sTNFR1 | -0.1 (0.4) | -0.1 (0.4) | -0.0 (-0.1 to 0.1) | 0.981 |
| sTNFR2 | -0.7 (0.3) | -0.7 (0.3) | -0.0 (-0.1 to 0.1) | 0.644 |
| TPSA | -0.2 (0.7) | -0.4 (0.7) | -0.3 (-0.5 to -0.1) | 0.012 |
| VEGF | 2.3 (0.6) | 1.9 (0.5) | -0.4 (-0.6 to -0.2) | 0.001 |
| vWF | -2.0 (0.3) | -1.9 (0.5) | 0.1 (-0.0 to 0.2) | 0.126 |

FIG. 2

| Biomarker | Con | TCC | AUC (95% CI) | Sensitivity (95% CI) | Specificity (95% CI) |
|---|---|---|---|---|---|
| BTA | 77 | 84 | 0.64 (0.55, 0.72) | 0.58 (0.48, 0.69) | 0.77 (0.67, 0.86) |
| CEA (serum) | 77 | 84 | 0.74 (0.67, 0.82) | 0.67 (0.57, 0.77) | 0.76 (0.67, 0.86) |
| CRP | 77 | 84 | 0.35 (0.26, 0.43) | 0.67 (0.57, 0.77) | 0.48 (0.37, 0.59) |
| D-Dimer | 77 | 84 | 0.65 (0.57, 0.74) | 0.52 (0.42, 0.63) | 0.78 (0.69, 0.87) |
| EGF | 77 | 82 | 0.39 (0.30, 0.47) | 0.38 (0.27, 0.48) | 0.71 (0.61, 0.81) |
| FAS | 77 | 82 | 0.65 (0.57, 0.74) | 0.58 (0.48, 0.69) | 0.74 (0.64, 0.84) |
| IL-1a | 76 | 84 | 0.65 (0.56, 0.73) | 0.61 (0.50, 0.71) | 0.64 (0.54, 0.75) |
| IL-1b | 76 | 84 | 0.56 (0.48, 0.65) | 0.36 (0.25, 0.46) | 0.80 (0.71, 0.89) |
| IL-2 | 76 | 84 | 0.60 (0.51, 0.68) | 0.63 (0.53, 0.73) | 0.55 (0.44, 0.66) |
| IL-4 | 77 | 84 | 0.54 (0.45, 0.63) | 0.40 (0.30, 0.51) | 0.80 (0.71, 0.89) |
| IL-6 | 76 | 84 | 0.68 (0.60, 0.77) | 0.67 (0.57, 0.77) | 0.70 (0.59, 0.80) |
| IL-8 | 76 | 84 | 0.70 (0.62, 0.78) | 0.68 (0.58, 0.78) | 0.68 (0.58, 0.79) |
| MMP/NGAL | 75 | 81 | 0.58 (0.49, 0.67) | 0.49 (0.39, 0.60) | 0.70 (0.60, 0.81) |
| VEGF | 76 | 84 | 0.68 (0.60, 0.77) | 0.63 (0.53, 0.73) | 0.64 (0.53, 0.75) |
| NMP22 | 39 | 67 | 0.73 (0.63, 0.82) | 0.58 (0.46, 0.70) | 0.87 (0.77, 0.98) |
| Cytology | 65 | 78 | 0.69 (0.60, 0.78) | 0.42 (0.31, 0.53) | 0.95 (0.90, 1.00) |
| Cystoscopy | 77 | 84 | N/A | 0.96 (0.92, 1.00) | 1.00 (1.00, 1.00) |

FIG. 3

| Correction | Correct classification/n | | AUC (95% CI) | Combination of biomarkers used in regression analysis |
|---|---|---|---|---|
| | Controls | TCCB | | |
| SPP | 48/77 (62%) | 68/81 (84%) | 0.785 (0.71, 0.86) | Age, smoking years, anti-hypertensive medication |
| None | 57/74 (77%) | 71/81 (88%) | 0.853 (0.79, 0.92) | SPP, VEGF, CEA, TUP |
| Protein | 61/75 (81%) | 71/81 (88%) | 0.871 (0.81, 0.93) | SPP, VEGF, CEA, MMP-9, IL-6 |
| Creatinine | 61/75 (79%) | 69/80 (86%) | 0.884 (0.83, 0.94) | SPP, VEGF, CEA, TM, NSE, D-dimer |
| Osmolality | 57/75 (76%) | 70/81 (86%) | 0.877 (0.82, 0.94) | SPP, VEGF, CEA, NSE, TM, IL-8 |
| None | 31/39 (80%) | 61/66 (92%) | 0.918 (0.86, 0.98) | SPP, NMP22, NSE, IL-4 |
| Protein | 30/39 (77%) | 62/65 (95%) | 0.909 (0.85, 0.97) | SPP, NMP22, MMP-9/NGAL |
| Creatinine | 32/39 (82%) | 63/66 (96%) | 0.928 (0.87, 0.98) | SPP, NMP22, TUP, IL-6, NSE |
| Osmolality | 32/39 (82%) | 63/66 (96%) | 0.928 (0.87, 0.98) | SPP, NMP22, TUP, IL-6, NSE |
| None | 55/75 (73%) | 66/82 (81%) | 0.812 (0.75, 0.88) | CEA, IL-8, NGAL |
| Protein | 58/75 (77%) | 65/82 (79%) | 0.828 (0.76, 0.89) | CEA, IL-8, NGAL, NSE, VEGF |
| Creatinine | 54/75 (72%) | 64/81 (79%) | 0.808 (0.74, 0.88) | CEA, IL-8, NGAL |
| Osmolality | 54/75 (72%) | 64/82 (78%) | 0.810 (0.74, 0.88) | CEA, IL-8, NGAL |
| None | 26/39 (67%) | 52/65 (80%) | 0.861 (0.79, 0.93) | NMP22, IL-2, EGF, NSE |
| Protein | 28/39 (72%) | 50/67 (75%) | 0.791 (0.71, 0.88) | NMP22, CEA |
| Creatinine | 27/39 (69%) | 56/65 (86%) | 0.865 (0.79, 0.94) | Fas, EGF, NSE, NMP22, CEA |
| Osmolality | 28/39 (72%) | 57/65 (88%) | 0.874 (0.80, 0.94) | CRP, NSE, IL-2, NMP22, CEA, FAS |
| None | 54/74 (73%) | 68/79 (86%) | 0.847 (0.78, 0.91) | SPP, CEA, VEGF |
| None | 30/38 (79%) | 58/64 (91%) | 0.899 (0.83, 0.97) | SPP, CEA, NMP22, VEGF |

METHOD FOR DETECTION OF, OR THE RISK OF, BLADDER CANCER

TECHNICAL FIELD

The present disclosure relates to methods of detecting the presence of, or the risk of, bladder cancer in a patient.

BACKGROUND

Bladder cancer is a leading cause of death worldwide. Bladder cancer is more than three times more common in men than women though the mortality rate in the latter is twice as great. Most of the patients who present with superficial bladder cancer tumours will experience a recurrence within 5 years and almost 90% of these patients will have a recurrence within 15 years. As such, it is vital that these patients are followed up on a regular basis to ensure that the cancer does not spread beyond the bladder. The constant monitoring and the costly diagnostic techniques results in bladder cancer being, on a cost per patient basis, the most expensive cancer to manage from diagnosis to death.

The usefulness of a diagnostic test is measured by its sensitivity and specificity. The sensitivity of a test is the number of true positives (the number of individuals with a particular disease who test positive for the disease) and the specificity is the number of true negatives (the number of individuals without a disease who test negative for the disease). The most common sign of bladder cancer is gross or microscopic haematuria, often detected by the family physician, and is observed in 85% of all bladder cancer patients. A simple urine dip test can be used to detect the presence of blood. Although cancer without blood is rare, leading to high sensitivity of a simply blood dip test, the specificity of the test is poor with fewer than 5% of patients presenting with haematuria actually having bladder cancer. However, the 5% of patients who do present are normally diagnosed with superficial tumours, which can easily be resected.

Cystoscopy and cytology are the preferred methods used to diagnose bladder cancer. A cytological examination involves the examination of urothelial cells in voided urine. This method has high specificity and it is convenient to obtain a sample. However, it has poor sensitivity and is subjective at low cellular yield. A cytological assessment is usually combined with flexibly cystoscopy. Cystoscopy allows direct observation of the bladder and biopsy of suspicious regions and results in 95% accuracy in diagnosis. It is therefore considered the gold standard in accurately diagnosing bladder cancer.

However, there are some disadvantages associated with cystoscopy, namely that it is extremely expensive, causes patient discomfort and does not allow for upper tract visualisation or for the detection of small areas of carcinoma in situ. Attempts have been made in the art to identify one or more biochemical bladder cancer biomarkers that could identify patients who present with bladder cancer before committing them to cystoscopy. At the present time approximately 20% of patients present with advanced disease and their prognosis is poorer as a result. Attempts have therefore been made in the art to identify a proven marker or panel of markers, which could be used as a screening tool for bladder cancer for high-risk asymptomatic patients.

No single biomarker or panel of biomarkers has yet achieved the levels of sensitivity and specificity required to reduce the frequency of cystoscopy needed for an accurate diagnosis. Over the last 10 years a large number of bladder cancer markers including BTA STAT, NMP22, telomerase and FDP, have been evaluated against the gold standard urine cytology with quite consistent results of low specificity. These markers are present in urine in a large proportion of patients with urological pathologies other than bladder cancer and in patients with urinary infections. NMP22 and BTA have FDA approval as point of care assays. However, NMP22 requires immediate stabilisation in urine, which is not always possible, and the presence of BTA can be masked by blood present in the urine. New putative markers, such as survivin, hyaluronic acid, cytokeratin 8 and 18 and EGF, which have been shown to induce expression of the matrix metalloproteinase (MMP9) in some bladder cancer cells have been proposed as bladder cancer markers. However, none of the putative biomarkers have been bench-marked against the high specificity of urine cytology and the high sensitivity of the telomerase assay.

Thus, in the field of bladder cancer diagnosis and treatment, the biomarkers identified in the prior art are unsatisfactory since they lack the required sensitivity and specificity required to make an accurate diagnosis of bladder cancer or assessment of a patient's risk in developing the disease. As a result the clinician is not able to accurately assess whether a patient should be put forward for further cytoscopic and cytological tests which results in high costs associated with diagnosing and managing the disease. An aim of the present disclosure is to overcome these problems.

SUMMARY

The aim of the present disclosure is to identify biomarkers that can be used to either diagnose bladder cancer as an adjunct to cytology by replacing cystoscopy or to diagnose bladder cancer as a self-contained test. The inventors have discovered that particular combinations of biomarkers, known to be important in the biochemical pathways of bladder cancer development, are present in the blood and/or urine of patients with bladder cancer. Through statistical analysis of various combinations of these biomarkers, taking into account various known risk factors for bladder cancer, the inventors have discovered that the presence of particular combinations of these biomarkers in urine and/or blood samples show a strong correlation to those patients with bladder cancer. The present disclosure therefore describes specific biomarker combinations which can be used in the diagnoses of, or risk of, bladder cancer in a patient.

Thus, in one aspect the present disclosure provides a method for the detection of, or the risk of, bladder cancer in a patient, comprising the step of detecting the presence of at least two biomarkers selected from CEA, VEGF, IL-8, NGAL, NSE, IL-2, EGF, TM, d-Dimer, MMP-9, IL-6, IL-4, MMP-9/NGAL, FAS, CRP, TUP and NMP22 in one or more samples isolated from a patient wherein the presence of a combination of at least two of the biomarkers in the one or more samples indicates the presence or risk of bladder cancer.

DESCRIPTION

The following is a list of abbreviations used in the present specification:
AHM Anti-Hypertensive Medication
AUC Area Under Curve
BPH Benign Prostate Hyperplasia
BTA Bladder Tumour Antigen
CEA Carcinoembryonic Antigen CK-18 Cytokeratin 18
CRP C Reactive Protein
EGF Epidermal Growth Factor
FAS FAS Protein
FDP Fibrinocyte Derived Protein
FPSA Free Prostate Specific Antigen
HA Hyaluronic Acid
HRP Horse Radish Peroxidase
HsCRP High Sensitivity C-Reactive Protein
IL-2 Interleukin 2
IL-4 Interleukin 4
IL-6 Interleukin 6
IL-8 Interleukin 8
LR Likelihood Ratio
MCP Monocyte Chemotactic Protein
MMP9 Matrix Metalloprotein 9
MMP-9/NGALMatrix Metalloprotein 9/Neutrophil Gelatinase Associated Lipocalin Complex
NGAL Neutrophil Gelatinase Associated Lipocalin
NMP22 Nuclear Matrix Protein 22
NSE Neuron Specific Enolase
POC Point of Care
RCC Renal Cell Carcinoma
ROC Receiver Operating Curve
SD Standard Deviation
SDS-PAGE Sodium Dodecyl Sulphate-Polyacrylamide Gel Electrophoresis
sTNFR1 Soluble Tumour Necrosis Factor 1
sTNFR2 Soluble Tumour Necrosis Factor 2
SPP Starting Predicted Probability (Age, smoking years and anti-hypertensive medication)
TCCB Transitional Cell Carcinoma of the Bladder
TM Thrombomodulin
TPSA Total Prostate Specific Antigen
TUP Total Urinary Protein
UTI Urinary Tract Infection
VEGF Vascular Endothelial Growth Factor
vWF von WillebrandFactor The present disclosure is based on the finding that combinations of specific biomarkers present in blood and/or urine samples, isolated from a patient suffering from bladder cancer, enable an accurate diagnosis of bladder cancer to be made. This is advantageous since it decreases the need for invasive diagnostic procedures.

The combination of biomarkers selected for identification comprises at least two biomarkers. In one or more embodiments, the combination of at least two biomarkers are selected from the group consisting of CEA, VEGF, IL-8, NGAL, NSE, IL-2, EGF, TM, d-Dimer, MMP-9, IL-6, IL-4, MMP-9/NGAL, Fas, CRP, TUP and NMP22. In certain embodiments, the combination of biomarkers comprises three, four, five, six, seven, eight, nine, ten, eleven or more separate biomarkers. In other embodiments, the combination of biomarkers comprises no more than six biomarkers. In further embodiments, at least one of the at least two biomarkers is NMP-22. In particular embodiments, the combination of biomarkers is one or more of VEGF, TUP and CEA; VEGF, CEA, MMP-9 and IL-6; VEGF, CEA, TM, NSE and D-dimer; VEGF, CEA, NSE, TM and IL-8; NMP-22, NSE and IL-4; NMP-22 and MMP9/NGAL complex; CEA, IL-8 and NGAL; CEA, IL-8, NGAL, NSE and VEGF; NMP-22, IL-2, EGF and NSE, NMP-22 and CEA; FAS, EGF, NSE, NMP-22 and CEA; CRP, NSE, IL-2, NMP-22, CEA and FAS. In even further embodiments, the combination of biomarkers may be NMP-22, IL-6, NSE and TUP. In still further embodiments, the combination is CEA and VEGF or CEA, NMP22 and VEGF.

In certain embodiments of the present disclosure, the patient to be tested for the present or risk of bladder cancer presents with haematuria. The method of the present disclosure is advantageous as it is able to determine whether a patient presenting with haematuria, has blood in his urine because he suffers from bladder cancer or from some other cause. For example, blood may be present in the urine due to a urinary tract infection.

The biomarkers as disclosed herein may be detected in at least one sample that is isolated from the patient. In certain embodiments, at least one biomarker is detected in each of a first and second sample isolated from the patient. In one embodiment, the first sample is a urine sample and the second sample is a blood sample. In certain embodiments, the CEA biomarker is detected in a blood sample whereas the other biomarkers are detected in urine. The presence of the biomarkers in the sample may be determined by commercially available methods. Biochip Array Technology (Randox Laboratories Ltd., Crumlin, Northern Ireland, UK) may be used for the simultaneous detection of multiple analytes from a single patient samples of urine and/or blood. The technology is based on the Randox Biochip, a 9 mm$^2$ solid substrate supporting an array of discrete test regions with immobilized, antigen-specific antibodies.

In one embodiment, the combination of biomarkers has a sensitivity and specificity of at least approximately 70%. This means that out of 100 patients which have bladder cancer, approximately 70% of them will be correctly identified from the determination of the presence of a particular combination of biomarkers as positive for bladder cancer (sensitivity test) while out of 100 patients who do not have bladder cancer approximately 70% will accurately test negative for the disease (sensitivity test). In certain embodiments, the combination of biomarkers has a sensitivity of at least approximately 75%. In other embodiments, the sensitivity will be at least approximately 81%, and the specificity of at least approximately 0.75%, alternatively of at least approximately 0.80%.

The following Example, with reference to FIGS. 1 to 3, describes methods by which the biomarkers may be detected in a urine or blood sample isolated from a patient. The biomarkers which were identified were then analysed statistically in order to identify particular combinations of biomarkers which correlate with the presence of bladder cancer in a patient. The statistical analysis shows that particular combinations of biomarkers correlate with the presence of such biomarkers in patients with bladder cancer.

FIG. 1 shows a univariate analyses of significant differences in biomarker profiles of samples obtained from bladder cancer patients and controls (T-test);

FIG. 2 shows biomarker sensitivities and specificities as determined by the effect of the presence or absence of a particular biomarker on a combination of biomarkers; and FIG. 3 shows the results of binary logistic regression analysis of biomarkers which significantly contribute to the sensitivity of the combination of biomarkers.

EXAMPLES

Example 1

A preliminary study was carried out to ascertain which individual biomarkers are significantly altered in bladder cancer patients compared to a control and which variables act ask risk factors for bladder cancer. 77 patients (55 males; 22 females) were assigned to the control group on the basis of negative cystoscopy and no evidence of bladder cancer following other investigations. Their final diagnoses were as follows: no diagnosis (n=36), prostate benign hyperplasia (BPH) (n=13), stone (n=9), stone with inflammation (n=2), inflammation (n=4), prostate cancer (n=3), renal cell carcinoma (RCC) (n=2), stone with BPH (n=2), renal cyst (n=1), renal trauma (n=1), urinary tract infection (n=1), fistula (n=1), trauma (n=1), endometriosis (n=1), RCC with BPH (n=1), stone with UTI (n=1) and squamous cell metaplasia (n=1).

82 patients (67 males; 15 females) with pathologically proven bladder cancer at the time of sampling were assigned to the TCCB group. Seventeen patients with a history of TCCB were disease free at the time of sampling.

Cystoscopic was negative for bladder cancer for all of the controls and for 3/81 of patient with TCCB. Following cytological assessment, 56/65 controls and 25/76 bladder cancers were classified as "no evidence of malignancy"; 5/65 and 8/76 as "atypia"; 1/65 and 10/76 as "suspicious" and 1/65 and 33/76 as "malignant", respectively. Two controls, classified as malignant, had prostate cancer.

It was found that that anti-hypertensive medications ($p<0.001$, Chi Square) and anti-platelet medications ($p=0.027$, Chi Square) are high risk factors for bladder cancer. The following biomarkers were also found to be significantly higher in bladder cancer patients: BTA, CEA (serum), d-Dimer, FAS, IL-1$\alpha$, IL-6, IL-8, MMP-9/NGAL complex and VEGF ($p<0.020$; t-test). FPSA and TPSA ($p<0.05$; t-test). EGF ($p<0.05$; t-test) and CRP ($p<0.02$; t-test) are significantly lower in bladder cancer patients than in controls.

For individual biomarkers, sensitivities in detecting the presence of or risk of bladder cancer ranged from 33 to 68% and specificities from 48 to 95%. IL-8 had the highest sensitivity and cytology the highest specificity. Combinations of biomarkers not comprising NMP22 had sensitivities and specificities which ranged from 71 to 83% and 86 to 94%, respectively. Combinations of biomarkers created incorporating NMP22 had sensitivities and specificities, which ranged from 71 to 87% and 88 to 98%, respectively. The combinations of biomarkers with the highest sensitivity were based on normalised data and incorporated NMP22. The combinations of biomarkers with the highest specificity used creatinine or osmolality corrected data, and also incorporated NMP22. The combinations of biomarkers without NMP22 were very different to that of the combinations with NMP22.

It was found that combinations of biomarkers analysed in conjunction with low numbers of risk factor variables were more robust. Patient age, smoking years and whether or not patients were taking anti-hypertensive medication were variables which contributed strongly to the sensitivity and specificity of combinations of biomarkers in detecting the presence of risk of bladder cancer. NSE and MMP-9 levels were not significantly different when controls and TCCB were compared but they did contribute significantly to 9/17 and 1/17 of the biomarker combinations respectively. Neutrophil gelatinase-associated lipocalin (NGAL) levels were significantly higher in patients taking antihypertensive medication ($p=0.022$, t-test), but NGAL levels were not significantly different between controls and bladder cancer patients. When patients not taking anti-hypertensives were compared across control and bladder cancer groupings those who had cancer had smoked for significantly longer, had significantly higher levels of CEA, VEGF and NSE. When patients on anti-hypertensive medication were compared there were no significant differences between control and bladder cancers.

Example 2

From the preliminary results of Example 1a further investigation was made to find particular combinations of biomarkers which can be used to accurately diagnose the presence or risk of bladder cancer in a patient without the necessity of also ascertaining the patient's exposure to other risk factors during the clinical examination. The further investigation was designed to take in to account the effect the various risk factors identified in the preliminary investigation detailed above have on the presence of individual biomarkers in samples obtained from a patient tested for bladder cancer such that a series of specific biomarker combinations may be obtained which are reflective of various bladder cancer risk factors.

181 patients with a history of haematuria were recruited for a bladder cancer trial. All patients had undergone cytoscopic examination. Patients who were assigned to the control group had negative cystoscopy or subsequent normal pathology whilst those assigned to the transitional cell carcinoma of the bladder (TCCB) group had pathologically confirmed bladder cancer.

A number of risk factors are known in bladder cancer development. Age and smoking are the most accurate discriminating factors in determining whether a patient who presents with haematuria has bladder cancer or some other pathology. Therefore, in order that the combinations of biomarkers provide an accurate means of detecting the presence or risk of bladder cancer as opposed to another pathology which clinically presented as haematuria, the known risk factors were assessed in each patient and the affect on the presence of each of the proposed biomarker combinations taken in to account. Thus, all of the patients in the study were assessed for their exposure to various bladder cancer risk factors by answering a questionnaire at the beginning of the study. The questionnaire asked the patient's age and sex and whether there is a family history of bladder cancer. Other risk factors investigated were whether the patient suffers from renal stone disease, recurrent urinary infections, benign prostatic hypertrophy or malignant diseases and whether he had received pelvic radiotherapy. Of particular importance is whether the patient is a smoker and, if so, the length of time as a smoker and the quantity and type of tobacco smoked (pipe or cigarette), his alcohol consumption and medical history. The patient's medical history is of particular significant since a number of drugs are known to affect the expression of a number of the biomarkers in the patient's blood and/or urine. Drugs which have such an effect may be selected from anti-hypertensive drugs, anti-cholesterol drugs, anti-platelets drugs, anti-ulcer drugs, prostate reduction drugs, anti-asthma drugs, analgesic drugs, anti-depressant drugs, anti-inflammatory drugs, anti-diabetes drugs, anti-coagulant drugs, anti-anxiety drugs and vitamins.

The risk factors positively identified were assigned a starting predictive probability (SPP) which is an indicator of each risk factor's contribution to the development of bladder cancer in the patient. The SPP is based on the average value of each risk factor for a patient presenting with bladder cancer e.g. average age and average number of cigarettes smoked, which is shown in FIG. 1. As a result, the statistical analysis conducted on the various biomarker combinations discussed below takes into account the possible effect that each risk factor may have on the development of bladder cancer and the presence of a particular biomarker. Therefore, in the clinical setting the methods described in present disclosure may be used in the diagnosis of the presence or risk of bladder cancer by the determination of the presence of various combinations of biomarkers which specific combination is designed to already have taken into account the other possible risk factors for bladder cancer.

Urine samples (50 ml) and serum samples (2 ml) were collected from all patients in sterile containers. Unfiltered and uncentrifuged urine samples were immediately aliquoted at −80° C. until analyses. Urine samples were thawed on ice and then centrifuged (1200×g, 10 minutes, 4° C.) to remove any particulate matter prior to analysis. Immediately after collection, 15-20 ml of unfiltered and non-centrifuged urine was placed in a plain sterile container and stored at 4° C. until processing for routine cytological assessment within 24 h. The pathologist (NHS) reported preparations which were stained with Papanicolaou and Geimsa as either insufficient for analysis, normal, atypical, suspicious or malignant. The presence of inflammatory cells was also recorded. Haematoxylin and Eosin-stained tumour sections were graded, staged and assessed for inflammatory infiltrate by a pathologist. Patients designated as controls, newly diagnosed or recurrent TCCB were included in all analyses. Urine samples (2.5 µl/lane) from each of the patients were analysed using SDS PAGE (16%) analysis. The gels were stained in Coomassie Blue for 1 hour and then destained in Methanol/Acetic acid/Water (2:1:7) until background was clear.

Detection of the presence of the biomarkers in the samples was then conducted. All samples were run in triplicate and the results are expressed as mean+SD (n=3).

Randox Biochip Array Technology was used to detect the presence of various biomarkers. Following antibody activation with assay buffer, standards and samples were added and incubated at 37° C. for 60 minutes, then placed in a thermo-shaker at 370 rpm for 60 minutes. Antibody conjugates (HRP) were added and incubated in the thermo-shaker at 370 rpm for 60 minutes. The chemiluminescent signals formed after the addition of luminol (1:1 ratio with conjugate) were detected and measured using digital imaging technology and compared with that from a calibration curve to calculate concentration of the analytes in the samples. The analytical sensitivity of the biochip was as follows: IL-2 4.8 pg/ml, IL-4 6.6 pg/ml, IL-6 1.2 pg/ml, IL-8 7.9 pg/ml, VEGF 14.6 pg/ml, TNFα 4.4 pg/ml, IL-1 α 0.8 pg/ml, IL-1β 1.6 pg/ml, MCP-1 13.2 pg/ml, NSE 0.26 ng/ml, NGAL 17.8 ng/ml, sTNFR1 0.24 ng/ml, d-Dimer 2.1 ng/ml, TM 0.5 ng/ml, hsCRP 0.67 ng/ml, MMP9 3.03 ng/ml, sTNFR2 0.2 ng/ml. Functional sensitivity for CEA and PSA (free and total) were 0.2, 0.02 and 0.045 ng/ml, respectively The presence of NMP22 was determined by a NMP22 urine dip tests (Matritech Inc, Newton, Mass. 02460, USA) at the point of care (POC) according to manufacturers' instructions. This was a single test for each patient.

The presence of BTA (U/ml) in each urine sample was determined using a commercial quantitative BTA ELISA (Polymedco, Inc. 510 Furnace Deck Road, Cortlandt Manor, N.Y. 10567, USA) according to manufacturers' instructions.

The presence of vWF (I U/ml) in each urine sample was determined using a commercial quantitative ELISA from Randox Laboratories, Crumlin, Northern Ireland, UK according to manufacturers' instructions.

The presence of MMP9/NGAL (ng/ml) in each urine sample was determined using an ELISA from Randox Laboratories Ltd. Crumlin, Northern Ireland, BT29 4QY, UK.

The presence of Cytokeratin 18 (ng/ml) in each urine sample was determined using a commercially available quantitative ELISA from USCNLIFE Science & Technology Co. Ltd., A1709, Guangguguo, East Lake, Hi-Tech Zone, Wuham, 430074, China.

The presence of hyaluronic acid (ng/ml) in each urine sample was determined using a commercially available quantitative competitive ELISA from Echelon Biosciences Inc., 675 Arapeen Drive, Suite 302, Salt Lake City, Utah, 84108, US.

The presence of FAS (pg/ml) in each urine sample was determined using a commercially available ELISA from RayBio Inc., Norcross, Ga. 30092, US.

The presence of EGF (ng/ml) in each urine sample was determined using an EGF ELISA from Randox Laboratories Ltd. Crumlin, Northern Ireland, BT29 4QY, UK.

The presence of telomerase in each urine samples was determined in triplicate by RT-PCR using a commercially available quantitative Telomerase detection kit (MT3012) according to manufacturers instructions (Express Biotech International (EBI) 503 Gateway Drive West, Thurmont, Md. 21788, USA).

The hydration status of the patient and thus the urine sample may affect the detection of a biomarker. The urine sample was therefore standardised to take into account the variation in hydration level. The standardisation procedure involved adjustment for the creatinine level (µmol/L) and the total urinary protein concentration (TUP) (mg/ml). Creatinine (µmol/L) measurements were determined using a quantitative in vitro diagnostic kit from Randox Laboratories (Catalogue No CR3814), and the results were collected from a Daytona RX Series Clinical Analyser (Randox Laboratories Ltd). The creatinine assay is linear up to 66000 µmol/L and has a sensitivity of 310 µmol/L. Osmolality (mOsm) was determined using a Löser Micro-Osmometer (Type 15) (Löser Messtechnik, Berlin, Germany). The Osmometer was calibrated using three independent readings of distilled water (0.1 ml) and a 300-mOsm standard supplied with the instrument. Calibration was confirmed by measuring the mOsm of a freshly prepared 0.9% NaCl solution (mean 286+3 mOsm, n=3). Instrument calibration was also verified at the end of analysis using the same 0.9% NaCl solution (mean 280.3+0.58 mOsm, n=3) to check for drift. Urine protein levels (mg/ml) were determined using a Bradford Assay Reagent Kit ($A_{595}$nm) (Pierce, Rockford, Ill., USA) and BSA as standard (1 mg/ml). Patient samples (10 µl/patient) were mixed with Bradford Reagent (1 ml) and read on a Hitachi Spectrophotometer (Model No U-2800) at A595 nm. The protein levels in the urine samples were determined from a BSA calibration chart (0-5 mg/ml, n=3).

Osmolality (mOsm) were determined using a Löser Micro-Osmometer (Type 15) (Löser Messtechnik, Berlin, Germany). Urine protein levels (mg/ml) were determined using a Bradford Assay Reagent Kit ($A_{595}$nm) (Pierce, Rockford, Ill., USA) and BSA as standard (1 mg/ml).

FIG. 1 indicates the statistically significant biomarkers that were found in the patients' urine and blood samples as well as a statistical measure of the variation of protein concentration, creatinine levels and osmolality of the sample between control patients and bladder cancer patients. From these results, 23 biomarkers in urines and one, CEA, in serum were thought to be statistically significant. These individual biomarkers were selected for further investigation in to which combinations of biomarkers would accurately predict the presence or risk of bladder cancer having taking in to account the variation in presence of risk factors form patient to patient and the variation in protein concentration, osmolality and creatinine levels from one patient's sample to another.

Means of triplicate biomarker measurements for each identified biomarker were then transformed to achieve normal distributions. Separate variables were created for corrected biomarker levels which were derived from the means for each biomarker which was divided by protein, creatinine or osmolality concentrations, and then averaged or log transformed. Differences in biomarker levels between TCCB and controls were assessed using Student T-test and p=0.05 as the significance level. Biomarker sensitivities and specificities for bladder cancer were determined from ROC analyses. These results are shown in FIG. 2.

The significant biomarker combinations were determined using forward wald binary logistic regression analysis (cut off probability for case classification=0.5). The regression analysis was conducted using SPSS regression software. The starting predictive probability, derived from the t-test analysis of the risk factor and clinical information derived from the patient questionnaire was used as a first classifier to normalise the AUC biomarker data shown in FIG. 2. The AUC biomarker data was also further normalized to take into account variations in protein and creatinine levels and osmolality. Biomarker sensitivities and specificities for bladder cancer were determined from cross-tabulation tables. Cross tabulations of final diagnoses against expected bladder cancer predicted by each combination of biomarkers were calculated (predicted probability>0.50, with controls having a predicted probability≤0.50). These results are shown in FIG. 3.

15 biomarker combinations were shown to correlate with patients having bladder cancer.

Discussion

The present disclosure describes methods of identifying patients which have or are at risk of developing bladder cancer through the detection of specific combinations of biomarkers. The selection of the particular biomarkers which are included in each combination takes in to account various risk factors which are known to contribute to the development of bladder cancer and the effects these have on individual biomarker levels in the patient. As a result, the clinician is able to determine whether a patient presenting with haematuria has bladder cancer or some other ailment which presents with haematuria, merely by detecting the presence of one of the combinations of biomarkers from the patient's blood or urine without needing to take into account other bladder cancer risk factors.

The biomarker combinations could not have been predicted from the prior art which merely notes that certain biomarkers are involved in the biochemical pathways of bladder cancer development. The disclosure of the specific combinations of biomarkers of the present disclosure and their use in diagnosing the presence or risk of bladder cancer in a patient is therefore novel and unexpected.

The invention claimed is:

1. A method for the detection of bladder cancer or a risk of bladder cancer in a patient, comprising:
    assaying a serum sample obtained from the patient for the presence or absence of the biomarker CEA (carcinoembryonic antigen), wherein said assaying of the serum sample comprises the steps of: (i) bringing the serum sample and an antibody specific for the biomarker CEA into contact with each other, wherein the presence of the biomarker CEA in the serum sample creates an antibody-CEA biomarker complex, and (ii) detecting the antibody-CEA biomarker complex, wherein detecting the antibody-CEA biomarker complex indicates the presence of the biomarker CEA in the serum sample from the patient;
    assaying a urine sample obtained from the patient for the presence or absence of at least one biomarker selected from vascular endothelial growth factor (VEGF), interleukin 8 (IL-8), neutrophil gelatinase associated lipocalin (NGAL), neuron specific enolase (NSE), epidermal growth factor (EGF), thrombomodulin (TM), d-Dimer, matrix metalloprotein 9 (MMP-9), interleukin 6 (IL-6), FAS protein (FAS), total urinary protein (TUP), and nuclear matrix protein 22 (NMP22), wherein the at least one biomarker assayed in the urine sample does not include CEA, wherein said assaying of the urine sample comprises the steps of: (i) bringing the urine sample and an antibody specific for the at least one biomarker into contact with each other, wherein the presence of the at least one biomarker creates an antibody-biomarker complex for the at least one biomarker, and (ii) detecting the antibody-biomarker complex for the at least one biomarker, wherein detecting the antibody-biomarker complex for the at least one biomarker indicates the presence of the at least one biomarker in the urine sample from the patient; and
    providing the results of the assay for the presence or absence of the biomarker CEA in the serum sample and providing the results of the assay for the presence or absence of the at least one biomarker in the urine sample;
    wherein detecting the presence of the combination of the biomarker CEA in the serum sample and the at least one biomarker in the urine sample indicates bladder cancer or a risk of bladder cancer in the patient, wherein the combination of CEA and at least one other biomarker is selected from:
    VEGF, CEA and TUP;
    VEGF, CEA, MMP-9 and IL-6;
    VEGF, CEA, TM, NSE and d-Dimer;
    VEGF, CEA, NSE, TM and IL-8;
    CEA, IL-8 and NGAL;
    CEA, IL-8, NGAL, NSE and VEGF;
    NMP-22 and CEA;
    FAS, EGF, NSE, NMP-22 and CEA; or
    CEA and VEGF.

2. The method of claim 1, wherein the patient presents with hematuria.

3. The method of claim 1, wherein the combination of CEA and at least one other biomarker is VEGF, CEA and TUP.

4. The method of claim 1, wherein the combination of CEA and at least one other biomarker is VEGF, CEA, MMP-9 and IL-6.

5. The method of claim 1, wherein the combination of CEA and at least one other biomarker is VEGF, CEA, TM, NSE and D-dimer.

6. The method of claim 1, wherein the combination of CEA and at least one other biomarker is VEGF, CEA, NSE, TM and IL-8.

7. The method of claim 1, wherein the combination of CEA and at least one other biomarker is CEA, IL-8 and NGAL.

8. The method of claim 1, wherein the combination of CEA and at least one other biomarker is CEA, IL-8, NGAL, NSE and VEGF.

9. The method of claim 1, wherein the combination of CEA and at least one other biomarker is CEA and VEGF.

10. The method of claim 1, further comprising recommending cytoscopic testing for bladder cancer in the patient if CEA is indicated to be present in the serum sample and the at least one biomarker is indicated to be present in the urine sample.

11. The method of claim 1, further comprising obtaining the serum sample and urine sample from the patient prior to said assaying of the serum sample and said assaying of the urine sample.

12. The method of claim 1, wherein the combination of CEA and at least one other biomarker is NMP-22 and CEA.

13. The method of claim 1, wherein the combination of CEA and at least one other biomarker is FAS, EGF, NSE, NMP-22 and CEA.

* * * * *